(12) United States Patent
Romano et al.

(10) Patent No.: US 6,218,154 B1
(45) Date of Patent: Apr. 17, 2001

(54) ISOTHERMAL TRANSCRIPTION BASED ASSAY FOR THE DETECTION AND QUANTIFICATION OF CHEMOKINES RANTES, MIP-1α AND MIP-1β

(75) Inventors: Joseph W. Romano, Derwood, MD (US); Roxanne Shurtliff, Herndon; Kimberly G. Williams, Falls Church, both of VA (US)

(73) Assignee: Akzo Nobel N.V., Arnhem (NP)

( * ) Notice: Subject to any disclaimer, the term of this patent is extended or adjusted under 35 U.S.C. 154(b) by 0 days.

(21) Appl. No.: 09/356,281

(22) Filed: Jul. 16, 1999

Related U.S. Application Data

(62) Division of application No. 09/010,641, filed on Jan. 22, 1998, now Pat. No. 6,121,023.

(51) Int. Cl.$^7$ .................................................. C12P 19/34
(52) U.S. Cl. .......................... 435/91.2; 435/6; 435/91.1; 536/22.1; 536/23.1; 536/24.3; 536/24.31; 536/24.32; 536/24.33
(58) Field of Search ............................. 935/6, 91.1, 91.2; 530/22.1, 23.1, 24.3, 24.31, 24.36, 24.33

(56) References Cited

U.S. PATENT DOCUMENTS

| | | |
|---|---|---|
| 5,130,268 | 7/1992 | Malek et al. . |
| 5,234,809 | 8/1993 | Boom et al. . |
| 5,409,818 | 4/1995 | Davey et al. . |
| 5,554,517 | 9/1996 | Davey et al. . |
| 5,616,688 | 4/1997 | Cerami et al. . |
| 5,668,294 | 9/1997 | Meagher et al. . |
| 5,827,730 | * 10/1998 | Pedersen et al. ................. 435/320.1 |
| 5,834,255 | 11/1998 | Van Gemen et al. . |
| 5,856,301 | * 1/1999 | Craig et al. ........................... 514/12 |

FOREIGN PATENT DOCUMENTS

| | | |
|---|---|---|
| WO9205198 | * 4/1992 | (WO) . |
| WO 93 13663 | 7/1993 | (WO) . |
| WO 94 29345 | 12/1994 | (WO) . |
| WO95/04158 | * 2/1995 | (WO) . |
| WO 95 20681 | 8/1995 | (WO) . |
| WO 96 17935 | 6/1996 | (WO) . |
| WO 96 23068 | 8/1996 | (WO) . |
| WO 96 40162 | 12/1996 | (WO) . |
| WO 97/19696 | 6/1997 | (WO) . |

OTHER PUBLICATIONS

J. Strehlau et al., Proc. Natl. Acad. Sci. USA, 94(2), 695–700, (abstract only), 1997.
F. Burke et al., Cytokine, 8(7), 578–85, (abstract only), 1996.
S. Michelson et al., J. Virol., 71(9), 6495–6500, (abstract only), 1997.
Y. Natori et al., Clin. Exp. Immunol., 109(1), 143–148, (abstract only 1997).
M. Adachi et al., Int. Arch Allergy Immunol., 113(1–3), 307–311, (abstract only), 1997.
N. Powell et al., Eur. Respir. J., 9(12), 2454–2560, (abstract only), 1996.
M. Srivastava et al., Res. Comm. Mol. Pathol. Pharmacol., 93(3), 263–287,(abstract only), 1996.
S. Matsukura et al., J. Allergy Clin. Immunol., 98(6 Pt 1), 1080–87, (abstract only), 1996.
N. Berkman et al., Am. J. Respir. Crit. Care Med., 154(6 Pt 1), 1804–11 (abstract only), 1996.
W. Halford et al., J. Immunol., 157(8), 3542–3549, (abstract only), 1996.
H. Yamada et al., Int. Arch Allergy Immunol., 111(Supp 1), 19–21, (abstract only), 1996.
K. Lim et al., J. Immunol., 156(7), 2566–2570, (abstract only), 1996.
Z. Lummus et al., Toxicology, 111(1–3), 191–296 (abstract only), 1996.
B. Canque et al., Blood, 87(5), 2011–2019, (abstract only), 1996.
H. Nakajima et al., J. Immunol., 156(12), 4859–66, (abstract only), 1996.
M. Tran et al., Invest Ophthalmol Vis. Sci., 37(6), 987–996, (abstract only), 1996.
R. Alam et al., Am. J. Respir Crit. Care Med., 153, 1398–404, (abstract only), 1996.
M. Baba et al., Int. J. Cancer, 66(1), 124–129, (abstract only), 1996.
S. Ying et al., Eur. J. Immunol., 26(1), 70–76, (abstract only), 1996.
C. Power et al., Cytokine, 7(6), 479–482, 1995.
Y. Su et al., J. Virol., 70(2), 1277–1281, (abstract only), 1996.
J. Wang et al., Am. J. Respir Cell Mol. Biol., 14(1), 27–35, (abstract only), 1996.
C. Gelder et al., Thorax, 50(10), 1033–1037, (abstract only), 1995.
L. Zhou et al., Blood, 86(9), 3295–3301, (abstract only), 1995.
S. Matsukura et al., Arerugi, 44(7), 715–717, (abstract only), 1995.
K. Nadeau et al., Proc. Natl. Acad. Sci., USA, 92(19), 8729–33, (abstract only), 1995.
C. Melani et al., Int. J. Cancer, 62(5), 572–578, (abstract only), 1995.
R. Godiska et al., J. Neuroimmunol., 58(2), 167–176, (abstract only), 1995.

(List continued on next page.)

*Primary Examiner*—Kenneth R. Horlick
*Assistant Examiner*—Jeffrey Siew
(74) *Attorney, Agent, or Firm*—Michael G. Sullivan

(57) ABSTRACT

An isothermal transcription based amplification assay for the detection or quantification of chemokine RNA uses primers and probes for sequences within the gene for RANTES, MIP-1α and MIP-1 β. The quantitative system uses an internal control Q of a mutant version of each gene. Target specific primers and probes are also disclosed.

18 Claims, 4 Drawing Sheets

OTHER PUBLICATIONS

S. Hosaka et al., Clin Exp. Immunol., 97(3), 451–457, (abstract only), 1994.

I. Beckman et al., Cytokine, 6(2), 116–123, (abstract only), 1994.

A. Whyte et al., Lancet, 343(8908), 1291–1292, (abstract only), 1994.

Pattison et al., Lancet, 343(8891), 209–211, (abstract only), 1994.

P. Heeger et al., Kidney Int., 41(1), 220–225, (abstract only), 1992.

C. Plater–Zybrek et al., Immunology Letters, 57(1–3), 117–120, (abstract only), 1997.

M. Petrek et al., European Respiratory Journal, 10(6), 1207–1216, (abstract only), 1997.

J. Kim et al., J. of the Korean Soc. of Microbio., 30(60, 651–663, (abstract only), 1995.

D. Kuhn et al., Biochemical and Biophysical Research Communications, 211(1), 325–300, 1995.

D. Gilat et al., The Journal of Immunology, 4899–4906, 1994.

E. Scala et al., The Journal of Immunology, 4485–4492, 1997.

M. Coffey et al., Am. J. Physiol., 272, L1025–L1029, 1997.

T. Dragic et al., Nature, 381, 647–648, (abstract only), 1996.

F. Cocchi et al., Nature Medicine, 2(11), 1244–1247, 1996.

B. Premack et al., Nature Medicine, 2(11), 1174–1178, 1996.

M. D'Souza et al., Nature Medicine 2(12), 1293–1300, 1996.

W. Paxton et al., Nature Medicine, 2(4), 412–417, (abstract only), 1996.

Romano et al., "NASBA a Novel Isothermal Detection Technology for Qualitative and Quantitative HIV–1 RNA Measurements," Clinics in Laboratory Medicine, vol. 16, No. 1, Mar. 1996, pp. 89–103.

Natori et al., "Gene Expression of CC Chemokines in Experimental Cresentic Glomerulonephritis (CGN)," Clinical and Experimental Immunology, vol. 109, 1997, pp. 143–148.

Bisset et al., "Change in Circulating Levels of the Chemokines Macrophage Inflammatory Proteins I–Alpha and I–Beta, Rantes, Monocyte Chemotactic Protein–1 and Interkeukin–16 Following Severely Immunodeficient HIV–Infected Individuals with Indinavir," AIDS, vol. 11, No. 4, 1997, pp. 485–491.

Cocchi et al., "Identification of Rantes, MIP–1 Alpha, and MIP–1 Beta as the Major HIV–Suppressive Factors Produced by CD8–T Cells," Science, vol. 270, No. 572, 1995, pp. 1811–1815.

Schmidtmayerova et al., "Human Immunodificency Virus Type–1 Infection Alters Beta Peptide Expression in Human Monocytes into Brain and Lymph Nodes," Proc. Natl. Acad. Sci., USA, vol. 93, 1996, pp. 700–704.

Bluman et al., "Human Natural Killer Cells Produce Abundant Macrophage Inflammatory Protein–1 Alpha in Response to Monocyte–Derived Cytokines," Journal of Clinical Investigation, vol. 97, No. 12, 1996, pp. 2722–2727.

Pattison et al., "Rantes Chemokine Expression in Transplant–Associated Accelerated Atherosclerosis," Journal of Heart and Lung Transplantation, vol. 15, No. 12, 1996, pp. 1194–1199.

Strehlau et al., "Quantitative Detection of Immune Activation Transcripts as a Diagnostic Tool in Kidney Transplants," Proc. Natl. Acad. Sci. USA, vol. 94, 1997, pp. 695–700.

Schall et al., J. Immunology, vol. 141, pp. 1018–1025, 1988.

Ausubel et al., Current Protocols in Molecular Biology, section 4..03–4.5.2, 1988.

* cited by examiner

RANTES QT NASBA:
Performance in HIV-1+Patient PBMC

| Patient | Mean* | SD | Patient | Mean* | SD |
|---|---|---|---|---|---|
| 1 | 5.63 | 0.38 | 7 | 6.43 | 0.18 |
| 2 | 6.11 | 0.03 | 8 | 6.50 | 0.30 |
| 3 | 6.44 | 0.13 | 9 | 5.55 | 0.43 |
| 4 | 6.28 | 0.20 | 10 | 6.84 | 0.11 |
| 5 | 6.27 | 0.23 | 11 | 5.81 | 0.03 |
| 6 | 6.44 | 0.28 | 12 | 5.62 | 0.17 |

*Log mean value derived from individual analysis of $10^2, 10^3, 10^4$ PBMC per patient and results normalized to $10^4$ PBMC.

MIP-1 alpha QT NASBA:
Performance in HIV-1+Patient PBMC

| Patient | Mean* | SD | Patient | Mean* | SD |
|---|---|---|---|---|---|
| 1 | 4.76 | 0.00 | 7 | 6.00 | 0.19 |
| 2 | 5.10 | 0.06 | 8 | 5.57 | 0.12 |
| 3 | 4.80 | 0.06 | 9 | 5.13 | 0.03 |
| 4 | 6.16 | 0.09 | 10 | 5.74 | 0.08 |
| 5 | 5.85 | 0.06 | 11 | 5.40 | 0.30 |
| 6 | 5.87 | 0.10 | 12 | 6.07 | 0.15 |

*Log mean value derived from individual analysis of $10^4, 10^5,$ $10^6$ PBMC per patient and results normalized to $10^6$ PBMC.

MIP-1 beta QT NASBA:
Performance on In Vitro Produced RNA

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

ACCACACCCT GCTGCTTTGC CTACA                           25

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

AAACAGGCAA ATTTGTGTAA GTTCA                                                    25

(2) INFORMATION FOR SEQ ID NO:3:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:3:

TCACCCGAAA GAACCGCCAA                                                          20

(2) INFORMATION FOR SEQ ID NO:4:

(i) SEQUENCE CHARACTERISTICS:
                (A) LENGTH: 50 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:4:

AATTCTAATA CGACTCACTA TAGGGAAACA GGCAAATTTG TGTAAGTTCA                          50

(2) INFORMATION FOR SEQ ID NO:5:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:5:

TGCCCCGTGC CCACATCAAG GA                                                       22

(2) INFORMATION FOR SEQ ID NO:6:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:6:

TCACCCGAAA GAACCGCCAA                                                          20

(2) INFORMATION FOR SEQ ID NO:7:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:7:

TCACACAGGC ACCGAACCAA                                              20

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CCCAGAGAAG AAATGGGTTC GGGAG                                        25

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

AGAGCGAAGC TTCTGGACCC CTCAGGCA                                     28

(2) INFORMATION FOR SEQ ID NO:10:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

AATTCTAATA CGACTCACTA TAGGGAGAGC GAAGCTTCTG ACCCCTCAG GCA           53

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CATAGCTGAC TACTTTGAGA CGAGCAGCCA                                   30

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GAGGAGTGGG TCCAGAAATA TGTCA                                        25

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GGGAACATGC GTGTGACCTC CACA                                            24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TTGCCAAACA GCCACACTGT GGGA                                            24

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

ACAGGGGAAC TCTCAGAGCA AACAA                                          25

(2) INFORMATION FOR SEQ ID NO:16:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

AATTCTAATA CGACTCACTA TAGGGACAGG GGAACTCTCA GAGCAAACAA            50

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

ACACAGGCTG ATGACAGCCA CTCGG                                          25

(2) INFORMATION FOR SEQ ID NO:18:

(i) SEQUENCE CHARACTERISTICS:
        (A) LENGTH: 50 base pairs

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

AATTCTAATA CGACTCACTA TAGGGACACA GGCTGATGAC AGCCACTCGG          50

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

TTTCGATTTC ACAGTGTGTT TG                                        22

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TTTCGTCATT TATAGCGGTT TG                                        22

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CAGCACAGAC CTGCCGGCTT CGCTT                                     25

(2) INFORMATION FOR SEQ ID NO:22:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

AATTCTAATA CGACTCACTA TAGGGCAGCA CAGACCTGCC GGCTTCGCTT          50

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO:23:

CTGCAACCAG TTCTCTGCAT CACTTGCTGC                            30

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

CAAACCGCTA TAAATGACGA AA                                    22

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

CTTCTTAACT TAAATTTTAA TTTATT                                26

(2) INFORMATION FOR SEQ ID NO:26:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

GCGGAGAGGA GTCCTGAGTA TGGAGGAGA                             29

(2) INFORMATION FOR SEQ ID NO:27:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

AATTCTAATA CGACTCACTA TAGGGGCGGA GAGGAGTCCT GAGTATGGAG GAGA      54

(2) INFORMATION FOR SEQ ID NO:28:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

CTGTGGTATT CCAAACCAAA AGAAGCAAGC AA                                    32

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

ATCCTGGGTC CAGGAGTACG TGTA                                             24

(2) INFORMATION FOR SEQ ID NO:30:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TCACCTCTGA GAAAACCTCT TTTCCA                                           26

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

AGCTCTGCGT GACTGTCCTG TCTC                                             24

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

GAGGAAGCTT CCTCGCGGTG TA                                               22

(2) INFORMATION FOR SEQ ID NO:33:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

AATTCTAATA CGACTCACTA TAGGGGAGGA AGCTTCCTCG CGGTGTA                    47

(2) INFORMATION FOR SEQ ID NO:34:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:34:

GCTGGCTGGG AGCAGAGGCT GCTGG                                      25

(2) INFORMATION FOR SEQ ID NO:35:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

AATTCTAATA CGACTCACTA TAGGGGCTGG CTGGGAGCAG AGGCTGCTGG           50

(2) INFORMATION FOR SEQ ID NO:36:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

GCTAGTAGCT GCCTTCTGCT CTCCA                                      25

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

CTAGTAGCTG CCTTCTGCTC TC                                         22

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

CTAGTTCGAT TCGGTCCCTC TC                                         22

(2) INFORMATION FOR SEQ ID NO:39:

(i) SEQUENCE CHARACTERISTICS:
        (A) LENGTH: 22 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:39:

CTAGTAGCTG CCTTCTGCTC TC                                                 22

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

CTGCGTGACT GTCCTGTCTC                                                    20

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

GGAGAAGCAT CCGGGCTCAG GTGA                                               24

(2) INFORMATION FOR SEQ ID NO:42:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

AATTCTAATA CGACTCACTA TAGGGGGAGA AGCATCCGGG CTCAGGTGA                    49

(2) INFORMATION FOR SEQ ID NO:43:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

TTACTATGAG ACCAGCAGCC TCTGCTCCCA                                         30

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA -continued (xi) SEQUENCE DESCRIPTION: SEQ ID NO:44:

AATTCTAATA CGACTCACTA TAGGG                                      25

(2) INFORMATION FOR SEQ ID NO:45:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:45:

TTCTGAGTTC TGCAGCCTCA CC                                         22

ISOTHERMAL TRANSCRIPTION BASED ASSAY FOR THE DETECTION AND QUANTIFICATION OF CHEMOKINES RANTES, MIP-1α AND MIP-1β

This application is a divisional of U.S. application Ser. No. 09/010,641, filed Jan. 22, 1998 now U.S. Pat. No. 6,121,023 filed Sep. 19, 2000.

FIELD OF THE INVENTION

The present invention is directed to an isothermal transcription based assay for the detection and quantitation of the β chemokines regulated-upon-activation, normal T expressed and secreted (RANTES), macrophage inflammatory protein-1α (MIP-1α) and macrophage inflammatory protein-1β (MIP-1β). The present invention is also directed to oligonucleotides for amplifying chemokine RNA and probes for use in the detection and quantitation of the amplification product.

BACKGROUND OF THE INVENTION

The RANTES chemokine has been shown to be a potent inhibitor of HIV-1 infection (Cocchi et al, *Science* 270:1811, 1996). In this study it was shown that RANTES is one of the major suppressor factors produced by CD8+ cells. These suppressor factors have been implicated in the long term nonprogression of many asymptomatic HIV-1+ patients.

The invention described herein is a transcription based amplification method for the detection of the RANTES mRNA transcript, which will be detected in the PBL of HIV-1+ patients. The purpose of applying such an assay would be to determine the presence and level of the transcripts and use these results to predict prognosis and/or direct therapeutic management of the infected patient. The invention would involve primers that were found to be optimal for the detection/quantification of the RANTES transcript in vivo using NASBA. Qualitative and quantitative detection would involve the use of an internal control RNA standard. The preliminary sample processing and nucleic acid isolation would be as described by Boom et al. The detection technology would involve the colorimetric ELGA based system and the ECL based system.

The β chemokines MIP-1α, MIP-1 β and RANTES inhibit infection of CD4+ T cells by primary, non-syncytium-inducing HIV-1 strains at the virus entry stage, and also block env-mediated cell-cell membrane fusion. CD4+ T cells from some HIV-1-exposed uninfected individuals cannot fuse with NSI HIV-1 strains and secrete high levels of β-chemokines. Expression of the β-chemokine receptor CC-CKR-5 in CD4+, non-permissive human and non-human cells renders them susceptible to infection by NSI strains, and allows env-mediated membrane fusion. CC-CKR-5 is a co-receptor for NSI primary strains of HIV-1. (Dragic et al, *Nature*, 381:667 (1996)).

The super family of chemoattractant cytokines (chemokines) and their receptors are involved in inflammation and infection. The chemokines range in size from 68 to 120 amino acids (in the mature form) and can be divided into three classes based on variations in a shared cysteine motif. The largest group, the C—C, or β chemokines has nearly 20 members identified to date. The smallest group, the C class, has but one. The C-X-C, or α chemokine branch can be further subdivided into two groups based on structure and function. The largest of these groups contains proteins containing the E-L-R-C-X-C motif and the smaller group is made up of proteins without the E-L-R amino terminal to C-X-C.

The structural classes parallel function to a large extent in that most C-X-C chemokines with E-L-R are chemoattractants for neutrophils but not monocytes, whereas C—C chemokines generally attract monocytes and lymphocytes, but not neutrophils. Basopiuils and eosinophils are also affected predominantly by C—C chemokines. The C chemokine appears thus far to be lymphocyte specific.

A number of chemokine receptors have also been identified. These proteins are structurally related, with amino acid homology high in the transmembrane regions and some intracellular loops. There seems to be less homology at the N- and C-termini, and extracellular loops, which are presumed to be involved in ligand binding (N-terminal) and receptor specific interactions with signaling components.

Engagement of the chemokine receptors results ultimately in the movement of the cell. The steps of this process are thought to be: relay of information from the receptor through G-proteins; mobilization of intracellular second messengers; coordinated reorganization of the cytoskeleton; formation of focal adhesions and attachment to and detachment from the substrate with pseudopodial extension, and retraction to effect directional migration.

The involvement of the chemokines and chemokine receptors in HIV infection is beginning to be understood. It has been known for some time that binding of the viral glycoprotein gp120 to CD4 is not sufficient for viral fusion and entry, suggesting the need for an additional coreceptor for HIV infection. Isolates of HIV generally have a tropism for either transformed T-cells (T cell line tropic or simply T-tropic strains) or for monocytes or cultured macrophages, and primary T cells, but not transformed T cells (macrophage tropic). The difference in tropism appears to reside in the V3 region of the gp120.

It was also known that there were endogenous HIV suppressor factors secreted by CD8+ T cells that inhibited viral replication in CD4+ cells in vitro. The β chemokines RANTES, MIP-1α and MIP-1β have now been identified as soluble suppressors of macrophage-tropic, but not T cell line tropic, HIV infection in vitro. (reviewed in Premack, *Nature Medicine*, 2(11): 1174 (1996)).

It has been observed that the resistance of persons who remain uninfected despite multiple high-risk sexual exposures is associated with the activity of the C—C chemokines RANTES, MIP-1α and MIP-1β. The relative resistance does not extend to T-cell line-adapted strains (Paxton et al., *Nature Medicine*, 2(4): 412 (1996)). These results are consistent with a model in which CCR5 is a coreceptor (with CD4+) for macrophage tropic strains of HIV, and RANTES, MIP-1α and MIP-1β are also ligands to CCR5. It has been shown that RANTES, MIP-1α and MIP-1β block the entry of HIV-1 into cells (Cocchi et al, *Nature Medicine*, 2(11): 1244 (1996)).

Chemokine levels in infected patients are therefore very important in determining the course of the disease. Detecting and quantitating the RNA for the chemokines is therefore an important factor in the clinical evaluation of HIV positive patients.

Because chemokines are involved in the activation of inflammatory cells, previous workers have investigated the levels of chemokines or chemokine RNAs in different diseases or conditions related to inflammation. These diseases and conditions include graft rejection (Strehlau et al, *Proc. Nat Acad. Sci*. 94(2): 695–700 (1997)); cancer (Burket et al, *Cytokine* 8(7): 578–585, (1996)); HIV-1 infection (Schmidtmayerova et al, *Proc. Nat. Acad. Sci*. 93(2): 700–704, (1996)); human cytomegalovirus infection (Michelson et al, *J. Virol.* 71(9): 6495–6500 (1997)); asthma (Berkman et al, *Am. J. Respir. Crit. Care Med.* 154(6/1): 1804–11 (1996); and others.

Lastly, it may be easier to establish correlations between β-chemokines transcript levels and disease state due to the increased sensitivity of the amplification based transcript NASBA assay, and the typically larger dynamic range of the quantitative NASBA system.

An isothermal amplification method for detection or quantification of chemokine mRNAs has not been described.

SUMMARY OF THE INVENTION

The present invention provides isothermal transcription based amplification assays for the detection and quantitation of β chemokine RNAs. The detection assay uses primer pairs and probes for each of the targets, RANTES, MIP-1α and MIP-1β. Quantitative assays use an internal control RNA (Q) that differs from the wild type RNA by a small internal randomized segment. Q RNA is spiked into the sample at a known copy number at lysis and is coextracted and coamplified with wild type RNA. The resulting amplificate is then subjected to two independent hybridization reactions with probes specific for the wild type and Q amplificates. Quantitation of the wt RNA is achieved by calculating the ratio of resulting signal of wild type to Q.

An isothermal amplification method starts with an RNA template and alternately synthesizes DNA and RNA. Using an RNA template, a primer, and reverse transcriptase, an RNA/DNA hybrid is generated. The RNA is degraded from the hybrid by the RNAse H activity. A double stranded DNA is then generated by the reverse transcriptase using another primer, and then the double stranded DNA is used as template for large amounts of RNA synthesis by the RNA polymerase. One of the primers has, in addition to the sequences complementary to the template, additional sequences necessary for generating an RNA polymerase promoter and transcription initiation site which can be used by the RNA polymerase.

One of the advantages of an isothermal transcription based amplification method, as compared to other amplification methods such as PCR, is that by being essentially isothermal, it requires few manipulations by the experimenter. The method may be used on purified or semi-purified RNA extracts, or on cell or tissue samples with in situ amplification. In addition, if the sample contains both DNA and RNA, the use of RT/PCR requires a first step of DNAse treatment, or some method to distinguish the amplification products of mRNA- and DNA-derived PCR products is necessary. DNAse treatment prior to RT-PCR can be employed (Bitsch, A. et al., *J. Infect. Dis.* 167, 740–743, 1993; Meyer, T. et al., *Mol. Cell Probes*, 8, 261–271, 1994), but sometimes fails to remove contaminating DNA sufficiently (Bitsch, A. et al., 1993).

The purpose of applying such an assay would be to determine the presence and level of these transcripts, and to use these levels as prognostic makers (in conjunction with other disease makers) and/or to direct therapeutic management of the infected patient.

DETAILED DESCRIPTION OF THE INVENTION

Figure 1:
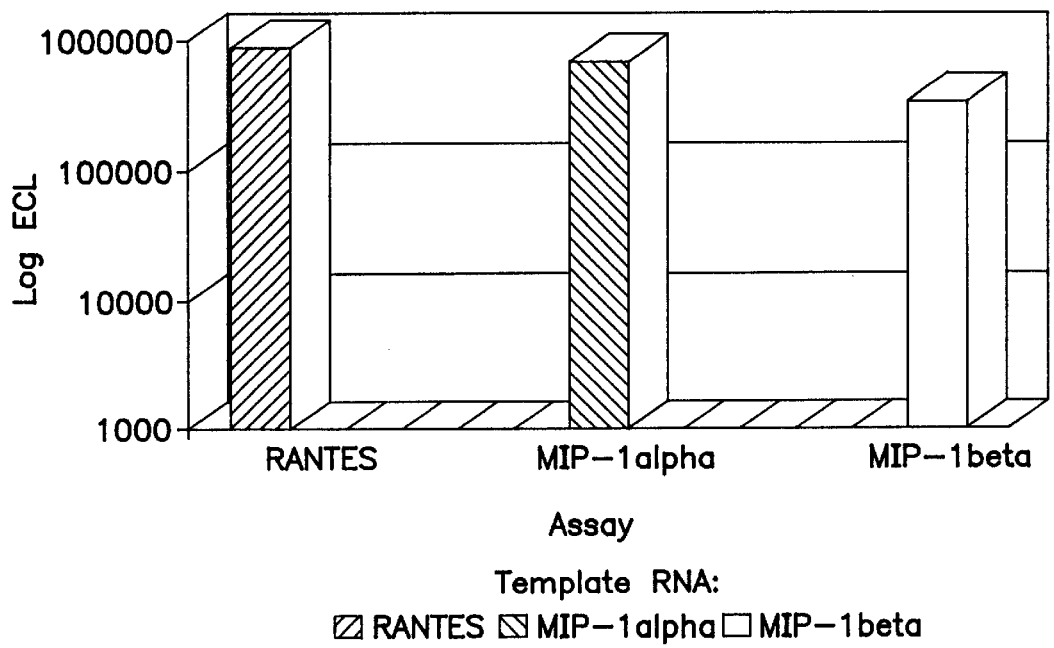
FIG. 1 shows the specificity of the NASBA chemokine RNA assays discussed in Example 5.

An isothermal transcription based assay is used for the detection and quantitation of RANTES, MIP-1α and MIP-1β RNAs. Any isothermal transcription based assay may be used with the primers and probes of the present invention. The isothermal transcription based assay of the present invention is carried out under conditions that can be readily determined by a person of ordinary skill in the art.

The preferred amplification method of the present invention is the isothermal transcription based amplification system referred to as NASBA. The NASBA method is disclosed in U.S. Pat. Nos. 5,409,818 and 5,554,527, which are herein incorporated by reference. NASBA includes the use of T7 RNA polymerase to transcribe multiple copies of RNA from a template including a T7 promoter.

Another technique for the amplification of nucleic acid is the so-called transcription based amplification system (TAS). The TAS method is described in International Patent Application No. WO 88/10315. Transcription based amplification techniques usually comprise treating target nucleic acid with two oligonucleotides one of which comprises a promoter sequence, to generate a template including a functional promoter. Multiple copies of RNA are transcribed from said template and can serve as a basis for further amplification.

Other transcription based amplification techniques are described in EP 408295. EP 408295 is primarily concerned with a two-enzyme transcription based amplification method. Transcription based amplification methods, such as the NASBA method described in EP 329822, are usually employed with a set of oligonucleotides, one of which is provided with a promoter sequence that is recognized by an enzyme with DNA dependent RNA polymerase activity such as, for example, T7 polymerase. Several modifications of transcription based techniques are known in the art. These modifications comprise, for example, the use of blocked oligonucleotides (that may be provided with a promoter sequence). These oligos are blocked so as to inhibit an extension reaction proceeding therefrom (U.S. Pat. No. 5,554,516). One or more "promoter-primers" (oligonucleotides provided with a promoter sequence) may be used in transcription based amplification techniques, optionally combined with the use of one or more oligonucleotides that are not provided with a promoter sequence.

The term "oligonucleotide" as used herein refers to a molecule comprised of two or more deoxyribonucleotides or ribonucleotides. Such oligonucleotides may be used as primers and probes.

Of course, based on the sequences of the oligonucleotides of the present invention, analogues of oligonucleotides can also be prepared. Such analogues may constitute alternative structures such as "PNA" (molecules with a peptide-like backbone instead of the phosphate sugar backbone of normal nucleic acid) or the like. It is evident that these alternative structures, representing the sequences if the present invention are likewise part of the present invention.

The term "primer" as used herein refers to an oligonucleotide either naturally occurring (e.g., as a restriction fragment) or produced synthetically, which is capable of acting as a point of initiation of synthesis of a primer extension product which is complementary to a nucleic acid strand (template or target sequence) when placed under suitable conditions (e.g., buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least 10 nucleotides in length of a sequence substantially complementary or homologous to the target sequence, but somewhat longer primers are preferred. Usually primers contain about 15–26 nucleotides but longer primers may also be employed, especially when the primers contain additional sequences such as a promoter sequence for a particular polymerase.

Normally a set of primers will consist of at least two primers, one "upstream" (P2) and one "downstream" (P1) primer which together define the amplificate (the sequence that will be amplified using said primers). One of the primers is understood to contain, in addition to sequences that will hybridize to the target sequence, sequences which provide promoter activity. Most often the P1 primer will include the promoter sequence.

The term "promoter sequence" defines a region of a nucleic acid sequence that is specifically recognized by an RNA polymerase that binds to a recognized sequence and initiates the process of transcription by which an RNA transcript is produced. In principle, any promoter sequence may be employed for which there is a known and available polymerase that is capable of recognizing the initiation sequence. Known and useful promoters are those that are recognized by certain bacteriophage RNA polymerases such as bacteriophage T3, T7 or SP6. Their function as a primer, e.g., the starting point for an elongation reaction, however, may be blocked, as already mentioned above, or absent in some embodiments of transcription based amplification reactions. A particularly preferred promoter sequence is the sequence of the T7 RNA polymerase promoter, the sequence of which is as follows: AATTCTAATACGACTCACTAT-AGGG SEQ ID NO:44.

SEQ ID NOs 4, 10, 16, 18, 22, 27, 33, 35, and 42 comprise the sequences of the specific target primer operably linked to the T7 promoter sequence, shown in italics. This makes the sequences especially suitable for use as downstream primer in a transcription based amplification technique such as NASBA. However, the sequences for the T7 promoter shown in italics may be substituted by seqeunces of other promoters for use with other RNA polymerases.

A preferred embodiment of the present invention is a combination of two oligonucleotides according to the invention, for use as a set in nucleic acid amplification.

One of the oligonucleotides may serve as an "upstream oligonucleotide", i.e., upstream primer, while the second oligonucleotide serves as a "downstream oligonucleotide", i.e., downstream primer, in the amplification reaction.

Preferably, the reverse transcriptase activity is provided by avian myeloblastosis virus (AMV) reverse transcriptase and the RNA polymerase is provided by T7 RNA polymerase.

One of the advantages of an isothermal transcription based amplification method, as compared to other amplification methods such as PCR, is that by being isothermal, it requires few manipulations by the experimenter. However, the absence of a high temperature step does make it somewhat more difficult to find appropriate primers (see below).

The amplification method of the present invention may be applied to extracts of samples comprising nucleic acid, or whole cells or tissues for in situ amplification. The samples may be various body fluids, particularly blood, plasma, and serum, from humans. The samples may also be tissue samples from humans, for instance, lymph tissue.

If the method is applied to extracts of samples comprising nucleic acids, the sample may be total RNA extracts (such as those described in Chomczynski and Sacchi, *Anal. Biochem.* 162:156, 1987) or "Boom" extracts (Boom et al, *J. Clin. Micro.*: 28, No.3, March 1990, p.495–503), which is herein incorporated by reference. The method is preferably applied to "Boom extracts".

The amplificate is detected by hybridization with an appropriately labeled oligonucleotide probe. The label may contain a radioactive moiety, a detectable enzyme, or any other moiety capable of generating a detectable signal, such as a colorimetric, fluorescent, chemiluminescent or electrochemiluminescent (ECL) signal. Blot based hybridization analysis and liquid hybridization based ECL analysis are preferably used, although other analysis systems such as ELGA (enzyme-linked gel assay) and in situ hybridization can also be used.

In one embodiment of the present invention, the amplification products are resolved by agarose gel electrophoresis, then transferred to nylon membranes and hybridized to a probe that is 5'-end labeled with $^{32}P$ using standard methods. The products are then visualized by autoradiography. In a second embodiment of the present invention, the amplification products can be detected using the ELGA. In this method the products of the amplification reaction are resolved on a polyacrylamide gel. A probe that is specific for the amplification reaction product and conjugated at its 5' end with horseradish peroxidase (HRP) is then hybridized. A calorimetric enzyme reaction allows for the visualization of the reaction product in the gel. A third embodiment of the present invention makes use of electrochemiluminescence chemistry (or ECL). This embodiment uses a biotinylated capture probe immobilized onto the surface of a streptavidin-coated magnetic bead via the biotin-avidin interaction. This system also requires an oligonucleotide detector probe, which can hybridize to an independent region of the amplification product. This detector probe is labeled with Ruthenium, the substance that is responsible for generating an ECL signal.

Each of the detection systems uses one or more internal controls to monitor the efficiency of the extraction process and the amplification assay itself. The detection systems are described in detail in Romano et al, *DNA Technology* 16:89–103 (1996), and van Gemen et al., *J. of Virol. Methods*, 49:157–168 (1994), which are herein incorporated by reference. Methods for internal controls are described in van Gemen et al, *Reviews in Medical Virology*, 5:205–211 (1995), which is herein incorporated by reference.

It may also be relevant to adapt the assay for an in situ format, which would be useful in pathology studies of tissue, particularly for lymphatic tissues. If the method is to be practiced on fixed preparations for in situ analysis, the method is performed as follows. Samples may include various body fluids or tissue samples. Lymph tissue is a preferred tissue for in situ analysis. The cells are fixed and then permeabilized to optimize permeability of the cell membranes. The fixatives are those standardly used in the art for cell or tissue preparations, such as acetone and methanol, ethanol, formalin, formaldehyde, paraformaldehyde, or Permafix®, and the permeabilization is done by proteinases, such as proteinase K or pepsinogen. The cells are then washed to remove all reagents that might inhibit the transcription based reaction. Permeabilization is done to the point that the cells allow entry of all necessary amplification reaction components, yet retain the targets and amplification products within the cells. In addition, cosolvents such as glycerol or DMSO may be added to optimize the NASBA reaction.

Detection of amplification products may be by direct labelling (with, for instance, biotin or digoxigenin—UTP) or by in situ hybridization with labelled probe. The direct labelling method requires that conditions can be optimized to remove unincorporated label while maintaining the amplification products.

In a particularly preferred embodiment of the present invention, the isothermal transcription based amplification method is used in concert with a particular RNA extraction technique ("Boom extraction", Boom et al, *J. Clin. Micro.*: 28, No.3, March 1990, p.495–503), and ECL detection (electrochemiluminescence). The advantages of the system are those associated with an amplification based assay capable of providing sequence level data. Although some of these same advantages exist for the RT-PCR (i.e., increased sensitivity over ELISA, gene sequence specificity), there are advantages of NASBA for RNA over RT-PCR. These include isothermal amplification, incorporation of reverse transcription into the amplification, application to wider array of specimen types (via Boom extract), and the sensitivity and dynamic range of the ECL detection.

Boom extracts are purified preparations of DNA and RNA. The Boom method is based on the lysing and nuclease inactivating properties of the chaotropic agent guanidinium thiocyanate (GuSCN) together with the nucleic acid binding properties of silica particles or diatoms. By using size fractionated silica particles, nucleic acids, including covalently closed circular, relaxed circular, linear double-stranded DNA, single stranded DNA, tRNA, mRNA, and rRNA, can be purified from a sample in less than one hour and recovered in the original reaction vessel.

A small sample is pipetted into a reaction vessel containing a solid nucleic acid carrier and a GuSCN containing lysis buffer. Lysis of the cells occurs and the released nucleic acids bind to the carrier. The carrier-nucleic acid complexes can be separated by centrifugation. Several wash steps follow and the complexes are then dried. The nucleic acids are eluted in an aqueous low-salt buffer in the initial reaction vessel and used for the amplification reaction.

In a preferred embodiment of the present invention, amplification is achieved in a 20 $\mu$L reaction containing 5 $\mu$L of the nucleic acid extract material in 10 $\mu$L of premix [Tris (40 mM) pH8.5; $MgCl_2$ (12 mM); KCl (70 mM); DTT (5 mM); dNTPs (each) (1 mM); rATP, rUTP, rCTP (2 mM); rGTP (1.5 mM); ITP (0.5 mM); DMSO (15%); P1 and P2, (0.2 $\mu$M); Sorbitol (1.5 M)]. This is then added to 5 $\mu$L of enzyme mix [BSA (2.1 $\mu$g/NASBA); RNase H (0.08 unit/NASBA); T7 RNA Polymerase (32 units/NASBA); and AMV-RT (6.4 units/NASBA)]. (The enzyme mixture must not be vortexed). If the nucleic acid sample decreases (5 $\mu$l), then the water volume increases accordingly so that the total volume stays 15 $\mu$l when the nucleic acid is added.

The method can be carried out as follows.
1. Mix premix.
2. Add 10 $\mu$l of premix to 5 $\mu$l of nucleic acid in an Eppendorf tube.
3. Incubate at 65° C. for 5 minutes.
4. Transfer to 41° C. heat block, incubate for 5 minutes.
5. Add 5 $\mu$l of enzyme mix.
6. Mix without vortexing.
7. Incubate at 41° C. for 5 minutes.
8. If the tops of the tubes have condensation from the cooling, they may be spun.
9. Incubate at 41° C. for 90 minutes.
10. Spin down samples and store at −20° C.

In the method of the present invention primers and probes were designed for the transcripts of RANTES, MIP-1α and MIP-1β. The primer and probe sequences were derived from the Genbank entries for these genes. A total of six primers were initially designed and synthesized; there was one primer combination for each of the three different target sequences. Subsequently additional primers and probes were also made. The primers- and probes are listed on Table 1.

TABLE 1

| Oligo (Map Site*) | Sequence (all listed 5'to 3') | |
|---|---|---|
| RANTES | | |
| P2A (88–112) | ACCACACCCTGCTGCTTTGCCTACA | SEQ ID NO:1 |
| P1A (296–320) | AAACAGGCAAATTTGTGTAAGTTCA | SEQ ID NO:2 |
| WT PROBE (194–213) | TCACCCGAAAGAACCGCCAA | SEQ ID NO:3 |
| P1A* | *AATTCTAATACGACTCACTATAGGG*AAACAGGCAAATTTGTGTAAGTTCA | SEQ ID NO:4 |
| P2B (125–146) | TGC CCC GTG CCC ACA TCA AGG A | SEQ ID NO:5 |
| WT PROBE (194–213) | TCA CCC GAA AGA ACC GCC AA | SEQ ID NO:6 |
| Q PROBE | TCA *CAC AGG CAC CGA* ACC AA | SEQ ID NO:7 |
| CAPTURE PROBE (225–249) | CCC AGA GAA GAA ATG GGT TCG GGA G | SEQ ID NO:8 |
| MIP-1α | | |
| P1A (273–296) | AGAGCGAAGCTTCTGGACCCCTCAGGCA | SEQ ID NO:9 |
| P1A* | *AATTCTAATACGACTCACTATAGGG*AGAGCGAAGCTTCTGGACCCCTCAGGCA | SEQ ID NO:10 |
| P2A (138–167) | CATAGCTGACTACTTTGAGACGAGCAGCCA | SEQ ID NO:11 |
| PROBE (232–256) | GAGGAGTGGGTCAGAAATATGTCA | SEQ ID NO:12 |
| P2C (349–372) | GGG AAC ATG CGT GTG ACC TCC ACA 3' | SEQ ID NO:13 |
| P2D (397–420) | TTG CCA AAC AGC CAC ACT GTG GGA 3' | SEQ ID NO:14 |

TABLE 1-continued

Oligonucleotides

| Oligo (Map Site*) | Sequence (all listed 5' to 3') | |
|---|---|---|
| P1C (500–524) | ACA GGG AAA CTC TCA GAG CAA ACA A3' | SEQ ID NO:15 |
| P1C* | AATTCTAATACGACTCACTATAGGGACAGGGGAACTCTCA GAGCAAACAA | SEQ ID NO:16 |
| P1D (561–585) | ACA CAG GCT GAT GAC AGC CAC TCG G | SEQ ID NO:17 |
| P1D* | AATTCTAATACGACTCACTATAGGGACACAGGCTGATGACAGCCACTCG G | SEQ ID NO:18 |
| PROBES | | |
| WT probe 2 (475–496) | TTT CGA TTT CAC AGT GTG TTT G | SEQ ID NO:19 |
| Q probe | TTT CGT CAT TTA TAG CGG TTT G | SEQ ID NO:20 |
| P1B (199–223) | CAGCACAGACCTGCCGGCTTCGCTT | SEQ ID NO:21 |
| P1B* | AATTCTAATACGACTCACTATAGGGCAGCACAGACCTGCCGGCTTCGCTT | SEQ ID NO:22 |
| P2B (51–80) | CTGCAACCAGTTCTCTGCATCACTTGCTGC | SEQ ID NO:23 |
| Antisense Q probe | CAA ACC GCT ATA AAT GAC GAA A | SEQ ID NO:24 |
| Capture probe (423–448) | CTT CTT AAC TTA AAT TTT AAT TTA TT | SEQ ID NO:25 |
| MIP–1β | | |
| P1A (346–374) | GCGGAGAGGAGTCCTGAGTATGGAGGAGA | SEQ ID NO:26 |
| P1A* | AATTCTAATACGACTCACTATAGGGGCGGAGAGGAGTC CTGAGTATGGAGGAGA | SEQ ID NO:27 |
| P2A (185–216) | CTGTGGTATTCCAAACCAAAAGAAGCAAGCAA | SEQ ID NO:28 |
| PROBE (237–260) | ATCCTGGGTCCAGGAGTACGTGTA | SEQ ID NO:29 |
| PRIMERS | | |
| P2C (33)–(-8) | TCA CCT CTG AGA AAA CCT CTT TTC CA | SEQ ID NO:30 |
| P2D (5–28) | AGCTCTGCGTGACTGTCCTGTCTC | SEQ ID NO:31 |
| P1D (112–133) | GAG GAA GCT TCC TCG CGG TGT A | SEQ ID NO:32 |
| P1D* | AATTCTAATACGACTCACTATAGGGGAG GAA GCT TCC TCG CGG TGT A | SEQ ID NO:33 |
| P1C (161–185) | GCT GGC TGG GAG CAG AGG CTG CTG G | SEQ ID NQ:34 |
| P1C* | AATTCTAATACGACTCACTATAGGGGCT GGC TGG GAG CAG AGG CTG CTG G | SEQ ID NO:35 |
| P2E (-50)–(-29) | TTC TGA GTT CTG CAG CCT CAC C | SEQ ID NO:45 |
| PROBES | | |
| WT probe 2 (36–60) | GCT AGT AGC TGC CTT CTG CTC TCC A | SEQ ID NO:36 |
| WT probe 2B (37–58) | CTA GTA GCT GCC TTC TGC TCT C | SEQ ID NO:37 |
| Q probe | CTA GTT CGA TTC GGT CCC TCT C | SEQ ID NO:38 |
| WT probe (37–58) | CTA GTA GCT GCC TTC TGC TCT C | SEQ ID NO:39 |
| Capture probe (9–28) | CTG CGT GAC TGT CCT GTC TC | SEQ ID NO:40 |
| P1B (312–335) | GGAGAAGCATCCGGGCTCAGGTGA | SEQ ID NO:41 |
| P1B* | AATTCTAATACGACTCACTATAGGGGGGAGAAGCATCCGGGCTCAGGTGA | SEQ ID NO:42 |
| P2B (150–179) | TTACTATGAGACCAGCAGCCTCTGCTCCCA | SEQ ID NO:43 |

*Position 1 is the A in the initiator codon.

EXAMPLE 1

NASBA-Initial Evaluation

A. Detection of Chemokine Transcripts By NASBA

Primers for RANTES (P1A/P2B for all cells except the B cells, which used P1A/P2A) and MIP-1α (P1A/P2A) were made and used in the standard NASBA assay on RNA prepared by the method of Chomczynski and Sacchi (1987) or by the method of Boom et al. (1990). Samples tested were HTLV-I chronically infected T-cells (MT2), HTLV-II chronically infected T-cells (MoT), HIV-1 chronically infected H9 cells (H9+), H9 cells, three patient PBMC sample (P1, P2, P3), PHA stimulated Peripheral Blood Mononuclear Cells (PBMC), enriched CD4+, CD8+, and B-cell populations, SF9 (negative control insect cells), human colon adenocarcinoma (COLO-205), human prostate adenocarcinoma (PC-3), and metastatic prostate adenocarcinoma (LNCAP). As shown on Table 2, almost all cell lines (other than the negative control, SF9) tested positive for both RANTES and MIP-1α.

TABLE 2

Detection of Chemokine Transcripts by NASBA

| Source | RANTES | MIP-1 alpha | Source | RANTES | MIP-1 alpha |
|---|---|---|---|---|---|
| MoT | pos | pos | PBMC | pos | pos |
| MT2 | pos | pos | CD4+ | pos | pos |
| H9+ | pos | pos | CD8+ | pos | pos |
| H9 | pos | neg | B cells | pos | pos |
| Colo 205 | pos | neg | Patient 1 | pos | pos |
| PC 3 | pos | pos | Patient 2 | pos | pos |
| LNCAP | pos | pos | Patient 3 | pos | pos |
| SF9 | neg | neg | | | |

B. Specificity of the MIP-1α and RANTES NASBA Assays

Wild type, in vitro produced RNA was obtained from plasmid constructs encoding the MIP-1α, RANTES, and MIP-1β cDNAs. Approximately $10^5$ copies of each of these RNAs were then amplified by NASBA with either the MIP-1α or RANTES primers, as above. Reaction products were then subjected to hybridization detection analysis using the ECL system, as well as $^{32}P$ labeled detector probes in Northern analysis. Each primer set was specific for the appropriate target RNA (data not shown).

C. RANTES WT and Q RNA NASBA Specificity

As shown in part A above, since it appeared that RANTES transcript was virtually ubiquitous, a quantitative assay was desired. Following the strategy outlined earlier, RANTES cDNA (WT) was cloned and mutagenized so as to produce the Q RNA calibrator. RNA was produced in vitro from both of these plasmid constructs. Further, ECL detection systems specific for RANTES WT and Q RNAs were developed. To evaluate this ECL system, $10^6$ copies of WT and Q RANTES RNAs were amplified by NASBA using the P1A/P2B primer pair. Resulting amplificates were analyzed by the WT and Q ECL detection system. Results show these probes are specific for WT and Q amplificates (data not shown).

D. RANTES WT and Q NASBA Sensitivity

The lower limit of amplification with the RANTES NASBA primer set was determined separately for in vitro RANTES WT and Q RNAs. Ten-fold dilutions of $OD_{260}$ quantified RNA (WT & Q) were amplified in separate NASBA reactions and analyzed with the ECL detection system. After correction for ECL background signal, it was demonstrated that amplification of both WT and Q RANTES RNAs was possible down to approximately 50 input copies (data not shown).

E. NASBA Coamplification of RANTES WT and Q RNA

In order to utilize an internal Q RNA standard for quantitative NASBA, it must be demonstrated that the amplification and detection efficiencies of the standard are sufficiently similar to the RNA analyte of interest. To this end, ten-fold dilutions of in vitro produced WT RANTES RNA were coamplified with either $2.5\times10^5$ or $2.5\times10^4$ copies of Q RNA. After coamplification, the reaction products were analyzed separately by ECL with WT and Q specific probes. The resulting ECL ratios were then used to calculate the WT copy number. Results demonstrated that the calculated copy number for the WT RNA was consistent in the undiluted sample. Further, the assay demonstrated ten-fold changes in RNA level, consistent with the dilution scheme used (data not shown).

F. Quantitation of Control RANTES RNA Subjected to Boom Extraction

Since actual clinical samples require a nucleic acid isolation step, the RANTES QT NASBA assay must be functional on material processed by the Boom method. This was demonstrated by essentially repeating the model system experiment described in section D, however the RNA mixtures were first subjected to coextraction, followed by coamplification. By establishing the ratio of WT RNA to the known Q RNA spike at the time of processing in lysis buffer, the assay is normalized for the potential loss of material during the course of the extraction procedure. The ECL ratios were used to calculate the WT RNA copy.

G. RANTES QT NASBA on PBMC and CEM

Once quantitation was shown to work satisfactorily with in vitro RNA model systems, PBMC and CEM (human carcinoma embryo) cells were analyzed. Ten-fold dilutions were made of each cell source in pH 6.2 GuSCN lysis buffer. A $2.5\times10^5$ Q spike was added to each dilution sample and subjected to coextraction by the Boom method. ECL signals for PBMC and CEM were used to quantitate WT RNA. Importantly, an approximate ten-fold change in WT RNA level was found, which is consistent with the ten-fold dilution scheme (data not shown).

EXAMPLE 2

RANTES

After looking at sequence comparisons with the MIPs and RANTES, P2B was designed to be less homologous to the MIP sequences. Sensitvity was tested and found to be the same as P2A, that is, 5 pg F3B (HTLV-1 transformed CD8+ cell line derived from an HIV-1 positive patient) total RNA. P1A/P2B was selected as the preferred primer set and all subsequent work was done with this set.

A. The primer oligonucleotides P1A and P2B were used with the Q control to quantitate RANTES in vitro produced RNA. In vitro transcribed RNA from the wild type gene as well as the Q gene was co-amplified with three different concentrations of the Q RNA. After amplification each mixture was measured by ECL with the correct probe.

Figure 2:
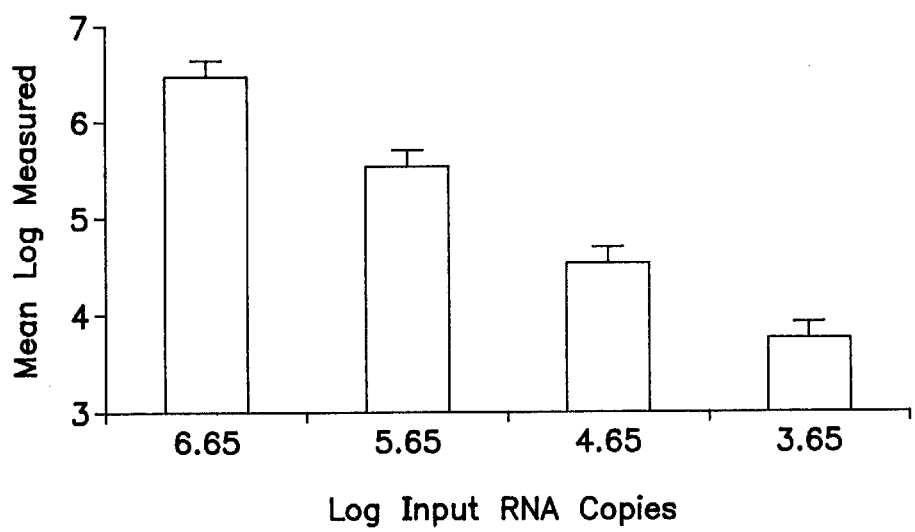
FIG. 2 shows the quantitation of RANTES in vitro transcribed RNA discussed in Example 2A.

The results are shown on FIG. 2. The mean log measured is proportional to the mean log input of RNA.

Figures 3, 4:
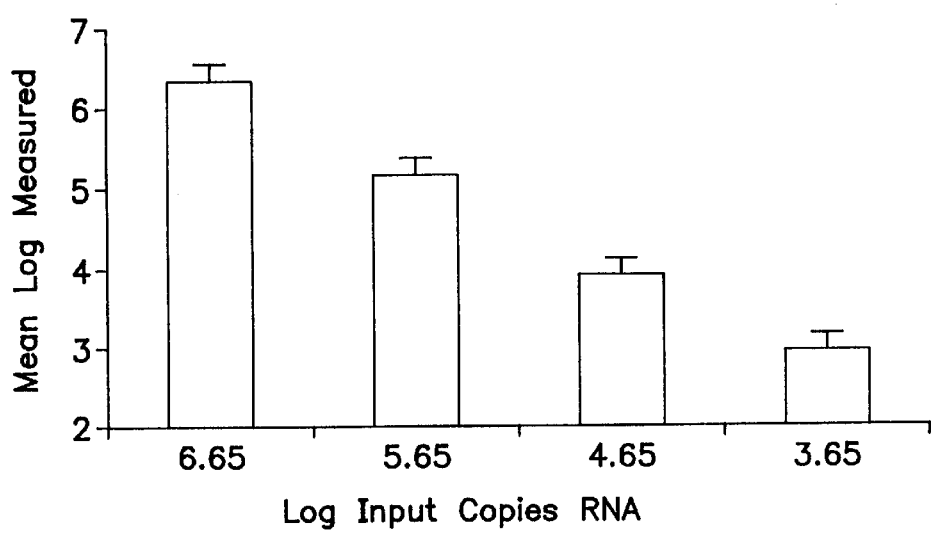
FIG. 3 shows the results of the RANTES NASBA assay on PBMCs from 12 HIV+ patients discussed in Example 2B.
FIG. 4 shows the quantitation of MIP-1α in vitro transcribed RNA discussed in Example 3B.

B. The same quantitative system was then used to measure RANTES RNA in dilutions of patient PBMCs. The PBMCs from twelve patients that were HIV-1+ as assessed by clinical diagnosis were used in a NASBA assay. RNA was extracted by the Boom method from the PBMCs and amplifications were performed on RNA from $10^4$ cells, $10^3$ cells, and $10^2$ cells for each patient. The log mean value was then derived from individual analysis of $10^4$, $10^3$, and $10^2$ PBMCs per patient and results normalized to $10^4$ PBMCs. These results are shown in FIG. 3.

C. Interestingly, the RANTES primer set will also amplify the simian version of this gene, suggesting that the invention may also be useful in monitoring suppressor factor production in animal model systems (data not shown).

EXAMPLE 3

MIP-1α

A. The sensitivity of the P1A/P2A primer pair was found to be 5 pg F3B total RNA. However, the primer pair did not demonstrate good in vitro RNA sensitivity. Additional primer pairs were designed and made. P1B/P2B were designed around the same area of the RNA as the P1A/P2A primer pair. Sensitivity was again found to be very poor. Additional primer pairs were designed and made in a separate region of the RNA. These latter primer pairs, P1C/P2C and P1D/P2D, showed good sensitivity, several orders of magnitude better than the prior pairs. P1C/P2C was selected for future use because there was more room for a capture probe with this pair.

B. The primer oligonucleotides P1C and P2C were used with the wt probe 2 and the Q control to quantitate MIP-1α in vitro produced RNA. In vitro transcribed RNA from the wild type gene as well as the Q gene was co-amplified with three different concentrations of the Q RNA. After amplification each mixture was measured by ECL with the correct probe. The results are shown on FIG. 4. The mean log measured is proportional to the mean log input of RNA.

Figures 5, 6:
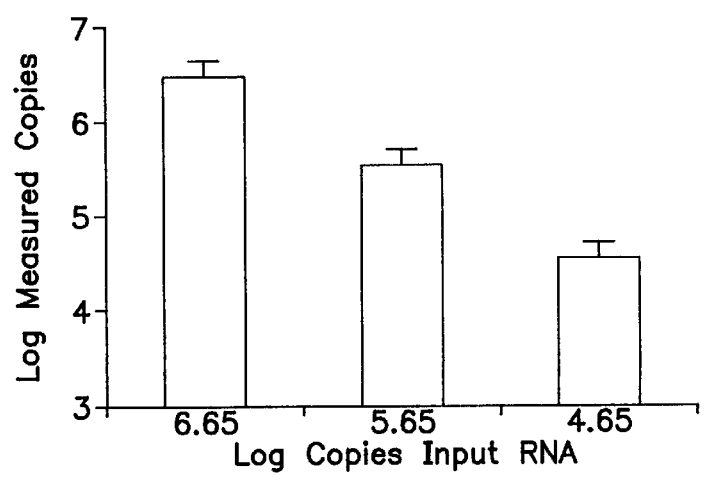
FIG. 5 shows the results of the MIP-1α NASBA assay on PBMCs from 12 HIV+ patients discussed in Example 3C.
FIG. 6 shows the quantitation of MIP-1β in vitro transcribed RNA discussed in Example 4B.

C. The same quantitative system was then used to measure MIP-1α RNA in dilutions of patient PBMCs. The PBMCs from twelve patients that were HIV-1+ as assessed by clinical diagnosis were used in a NASBA assay. RNA was extracted by the Boom method from the PBMCs and amplifications were performed on RNA from $10^6$ cells, $10^5$ cells, and $10^4$ cells for each patient. The log mean value was then derived from individual analysis of $10^6$, $10^5$, and $10^4$ PBMCs per patient and results normalized to $10^6$ PBMCs. These results are shown in FIG. 5.

EXAMPLE 4

MIP-1β

A. The first primer pair designed and made, P1A/P2A, was found to be of poor specificity. Even though the sequence did not predict such problems, the primer set amplified RANTES, MIP-1α and MIP-1β detected with the β probe.

A second set of primers was designed, made and tested. These primers, P1B/P2B, showed good specificity and acceptable sensitivity for in vitro transcribed RNA, but the primer set could not amplify cellular samples in NASBA.

Primers P1D, P2D, P2C were designed from a new area of the RNA. Both primer sets showed the same sensitivity. P1D/P2C was selected for additional work because the P2D could then be used as capture probe.

B. The primer oligonucleotides P1D and P2C were used with the Q control to quantitate MIP-1β in vitro produced RNA. In vitro transcribed RNA from the wild type gene as well as the Q gene was co-amplified with three different concentrations of the Q RNA. After amplification each mixture was measured by ECL with the correct probe. The results are shown on FIG. 6. The mean log measured is proportional to the mean log input of RNA.

Figure 7:
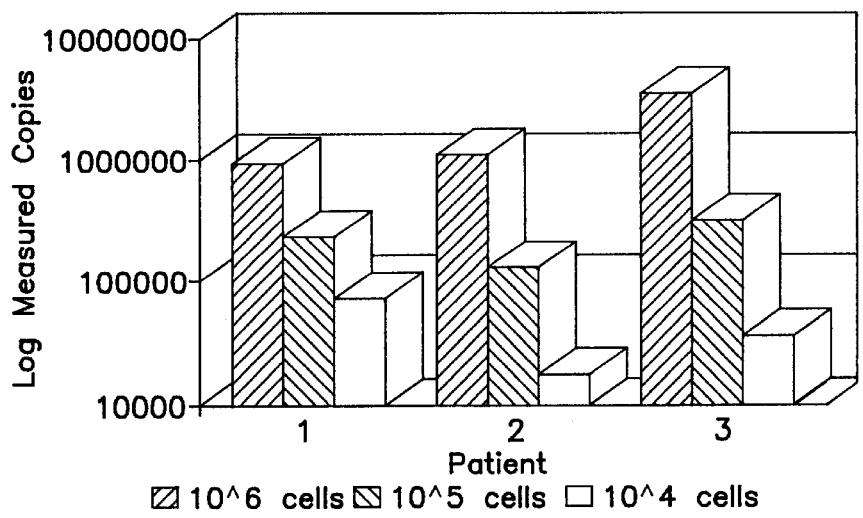
FIG. 7 shows the results of the MIP-1β NASBA assay on PBMCs from 3 HIV+ patients discussed in Example 4C.
Figure 8:
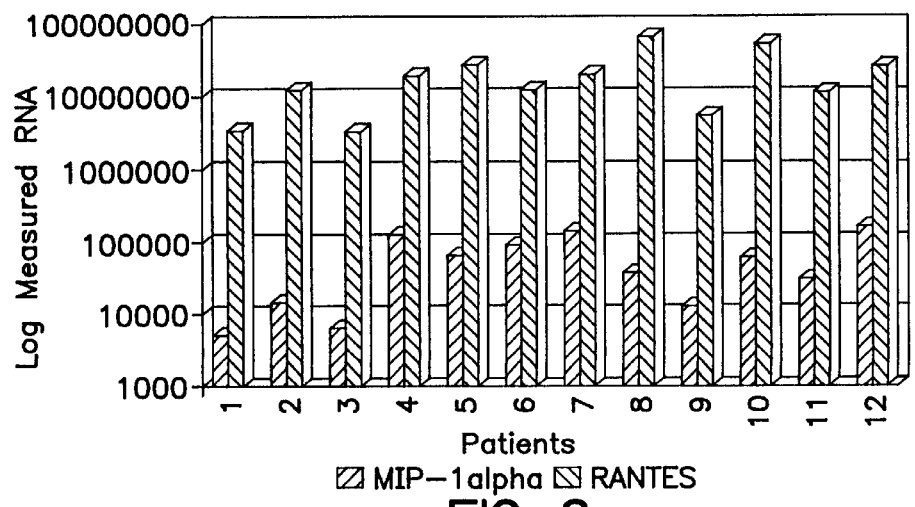
FIG. 8 compares the RANTES and MIP-1α RNA levels in HIV-1+ patients.

C. The same quantitative system was then used to measure MIP-1β RNA in dilutions of patient PBMCs. The PBMCs from three patients that were HIV-1+ as assessed by clinical diagnosis were used in a NASBA assay. RNA was extracted by the Boom method from the PBMCs and amplifications were performed on RNA from $10^6$ cells, $10^5$ cells, and $10^4$ cells for each patient. These results are shown in FIG. 7.

EXAMPLE 5

Specificity of the Preferred Primer Pair

The preferred primer pairs of Examples 2, 3, and 4 above were used to test the specificity of the NASBA assay of In vitro transcribed RNA. As shown in FIG. 1, each of the systems is specific for its target RNA.

The biggest problem encountered in the development of NASBA assays is the selection of primers. It has often been the case that primers selected from sequence data, and meeting all the known requirements for primers, do not actually function in practice (such as was the case with MIP-1α primers noted above). In addition, in some cases primers have been developed using model systems such as in vitro transcribed RNA, virus stocks, or cells lines with very high expression of the target gene, but those primers were found to be nonfunctional when the target molecule is in a background of clinical samples (such as was the case with the MIP-1β primers noted above). The exact mechanism underlying this problem is not understood, but is believed to arise due to the lower temperature of the NASBA reaction, which does not entirely melt secondary structure of the target molecule and/or allows nonspecific binding of primers to background nucleic acids in the sample. It is essential for the application of the NASBA system to clinical samples that the primers be not absorbed by background nucleic acids, but rather be available for specific binding to the target molecule.

The results shown in the present application demonstrate that the primers and probes of the present invention can specifically detect low levels of target molecules, even in the background of clinical samples. In addition, the primers should amplify the Q RNA and the Q and wt probes show appropriate specificity for their cognate targets. Thus, the primers used in the present invention provide unexpectedly good results for the detection and quantitation of β chemokine RNA.

Even though the non-preferred primers of the present invention are non-preferred for a NASBA method, such primers may be useful for other amplification methods such as polymerase chain reaction (PCR) or reverse transcription/polymerase chain reaction (RT/PCR).

Interestingly, we have shown that the expression of mRNA encoding chemokines (e.g., RANTES, MIP-1a, MIP-1b) can be detected in patient PBMC without the need for stimulation by mitogens. Since PBMC samples examined to date for MDC indicate the need for preliminary stimulation, it follows that the expression of different chemokine genes is not regulated in the same way. Thus, assays with detection and quantitation ability for chemokine RNA expression will be highly relevant to the overall assessment of patient immunocompetence.

---

We claim:

1. A method for the detection or quantitation of MIP-1β RNA in a sample comprising:
   a) obtaining a sample which may contain MIP-1β RNA;
   b) performing isothermal transcription based amplification on the sample with two oligonucleotide primers, a first primer which comprises at least 10 consecutive nucleotides of a sequence selected from the group consisting of SEQ ID NO:26, SEQ ID NO:32, SEQ ID NO:34, and SEQ ID NO:41, and a second primer which comprises at least 10 consecutive nucleotides of a sequence selected from the group consisting of SEQ ID NO:28, SEQ ID NO:30; SEQ ID NO:31, SEQ ID NO:43, and SEQ ID NO:45; and
   c) detecting or quantitating the resulting product of step b) whereby detection or quantitation of the amplification product indicates the presence or quantity of MIP-1β RNA in the sample.

2. The method of claim 1, wherein detection of the amplification product uses a labeled wild-type probe comprising a sequence selected from the group consisting of SEQ ID NO:29, SEQ ID NO:36, SEQ ID NO:37, and SEQ ID NO:39, whereby hybridization of the wild-type probe to the amplification product indicates the presence of MIP-1β RNA in the sample.

3. The method of claim 2, wherein detection of the amplification product further uses a capture probe according to SEQ ID NO:40.

4. The method of claim 1, further comprising adding a known amount of control RNA Q at step b), and detecting amplification product of Q by using a labeled probe comprising the sequence of SEQ ID NO:38, whereby the quantity of MIP-1β RNA in the sample is calculated by comparing the signals of the probes for Q and the wild-type probe.

5. The method of claim 1, wherein the sample comprises cells and RNA is extracted from the cells in the sample prior to step b).

6. The method of claim 1, wherein the first primer further comprises an RNA polymerase promoter sequence covalently bonded to the 5' end thereof.

7. The method of claim 6, wherein the RNA polymerase promoter sequence is SEQ ID NO:44.

8. An oligonnucleotide selected from the group consisting of SEQ ID NO:26–SEQ ID NO:43 and SEQ ID NO:45.

9. An oligonucleotide of 10–50 nucleotides, comprising at least 10 consecutive nucleotides of a sequence selected from the group consisting of SEQ ID NO:26, SEQ ID NO:28, SEQ ID NO:30, SEQ ID NO:31, SEQ ID NO:34, SEQ ID NO:36, SEQ ID NO:37, SEQ ID NO:38, SEQ ID NO:39, SEQ ID NO:40, and SEQ ID NO:41.

10. The oligonucleotide of claim 9, comprising at least 10 consecutive nucleotides of a sequence selected from the group consisting of SEQ ID NO:26, SEQ ID NO:28, SEQ ID NO:30, SEQ ID NO:31, SEQ ID No;34, and SEQ ID NO:41.

11. The oligonucleotide of claim 9, comprising at least 10 consecutive nucleotides of a sequence selected from the group consisting of SEQ ID NO:26, SEQ ID NO:34 and SEQ ID NO:41, further comprising an RNA polymerase promoter sequence covalently bonded to the 5' end thereof.

12. The oligonucleotide of claim 11, wherein the RNA polymerase promoter sequence is SEQ ID NO:44.

13. A primer pair for the detection or quantitation of MIP-1β RNA in a sample, comprising a first primer selected from the group consisting of SEQ ID NO:26, SEQ ID NO:27, SEQ ID NO:32, SEQ ID NO:33, SEQ ID NO:34, SEQ ID NO:35, SEQ ID NO:41, and SEQ ID NO:42, and a second primer selected from the group consisting of SEQ ID NO:28, SEQ ID NO:30; SEQ ID NO:31, SEQ ID NO:43, and SEQ ID NO:45.

14. The primer pair of the claim 13, comprising SEQ ID NO:30 and SEQ ID NO:32.

15. A kit for the detection or quantitation of MIP-1β RNA in a sample, comprising the primer pair of claim 13 and at least one probe selected from the group consisting of SEQ ID NO:29, SEQ ID NO:36, SEQ ID NO:37, SEQ ID NO:38, SEQ ID NO:39, and SEQ ID NO:40.

16. An oligonucleotide of 10–50 nucleotides, comprising at least 10 consecutive nucleotides of a sequence selected from the group consisting of SEQ ID NO: 32, further comprising an RNA polymerase promoter sequence covalently bonded to the 5' end thereof.

17. The oligonucleotide of claim 16, wherein the RNA polymerase promoter sequence is SEQ ID NO:44.

18. An oligonucleotide of 15–26 nucleotides, comprising at least 10 consecutive nucleotides of a sequence selected from the group consisting of SEQ ID NO:29, SEQ ID NO:32 and SEQ ID NO:4.

\* \* \* \* \*

UNITED STATES PATENT AND TRADEMARK OFFICE
CERTIFICATE OF CORRECTION

PATENT NO. : 6,218,154 B1
DATED : April 17, 2001
INVENTOR(S) : Romano et al.

It is certified that error appears in the above-identified patent and that said Letters Patent is hereby corrected as shown below:

<u>Claim 18,</u>
Please correct the last line, by replacing "SEQ ID NO: 4" with -- SEQ ID NO: 45 --.

Signed and Sealed this

Twenty-ninth Day of January, 2002

Attest:

Attesting Officer

JAMES E. ROGAN
*Director of the United States Patent and Trademark Office*